US00PP30905P2

(12) United States Plant Patent
Jachertz

(10) Patent No.: US PP30,905 P2
(45) Date of Patent: Sep. 24, 2019

(54) **X *GASTERALOE* PLANT NAMED 'D DELTA'**

(50) Latin Name: ***xGasteraloe* hybrid**
Varietal Denomination: D Delta

(71) Applicant: Christian Jachertz, Amposta (Tarragona) (ES)

(72) Inventor: Christian Jachertz, Amposta (ES)

(73) Assignee: Deltacactus S.L., Amposta (ES)

( * ) Notice: Subject to any disclaimer, the term of this patent is extended or adjusted under 35 U.S.C. 154(b) by 0 days.

(21) Appl. No.: 15/999,918

(22) Filed: Aug. 29, 2018

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
See application file for complete search history.

(56) References Cited

U.S. PATENT DOCUMENTS

PP29,138 P2 * 3/2018 van Langen ..... A01H 5/12
Plt./373

* cited by examiner

*Primary Examiner* — Susan McCormick Ewoldt

(57) ABSTRACT

A new cultivar of x *Gasteraloe* plant named 'D Delta' that is characterized by green leaves with green-white orbicular dots, leaf margins with white teeth and a star shaped basal rosette plant shape.

1 Drawing Sheet

Botanical classification: x *Gasteraloe* hybrid.
Variety denomination: 'D Delta'.

BACKGROUND OF THE INVENTION

The present invention relates to a new and distinct cultivar of x *Gasteraloe* plant botanically known as x *Gasteraloe* hybrid and hereinafter referred to by the cultivar name 'D Delta'.

'D Delta' originated from the crossing of the female or seed parent, an unnamed *Aloe aristata* cultivar with the male or pollen parent, an unnamed *Gasteria carinata* var. *verrucosa* cultivar. The crossing was conducted in 2013 in a greenhouse environment of Amposta, Tarragona, Spain. The resulting seeds were subsequently planted and grown in a greenhouse environment. The cultivar 'D Delta' was selected by the inventor in 2014 as a single plant within the progeny of the stated cross in a cultivated area of Amposta, Tarragona, Spain.

Asexual reproduction of the new cultivar 'D Delta' first occurred by leaf cuttings in 2015 in Amposta, Tarragona, Spain. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new x *Gasteraloe* cultivar 'D Delta'. These traits in combination distinguish 'D Delta' as a new and distinct cultivar apart from other existing varieties of x *Gasteraloe* known by the inventor.

1. x *Gasteraloe* 'D Delta' exhibits green leaves with green-white orbicular dots.
2. x *Gasteraloe* 'D Delta' exhibits leaf margins with white teeth.

3. x *Gasteraloe* 'D Delta' exhibits a star shaped basal rosette plant shape.

The closest comparison cultivars are *Gasteria* 'WT10' (U.S. plant Pat. No. 23,622) and plants of the species *Gasteraloe beguini*. 'D Delta' is distinguishable from 'WT10' by the following characteristics:

1. x *Gasteraloe* 'D Delta' exhibits darker green leaves than the leaves of 'WT10'.
2. x *Gasteraloe* 'D Delta' exhibits orbicular leaf dots that are more intense or brighter green-white in color than the leaf dots of 'WT10'.
3. x *Gasteraloe* 'D Delta' exhibits several plantlets at the base of mature plants. In contrast 'WT10' does not develop plantlets.

'D Delta' is distinguishable from plants of the species *Gasteraloe beguinii* by the following characteristics:

1. *Gasteraloe* 'D Delta' exhibits darker green leaves than the leaves of plants of the species *Gasteraloe beguinii.*
2. *Gasteraloe* 'D Delta' exhibits shorter and wider leaves than the leaves of plants of the species *Gasteraloe beguinii.*
3. *Gasteraloe* 'D Delta' exhibits leaves having smaller orbicular dots than the dots on leaves of plants of the species *Gasteraloe beguinii.*
4. x *Gasteraloe* 'D Delta' exhibits a smaller overall size than plants of the species *Gasteraloe beguinii*. Plants of the species *Gasteraloe beguinii* are larger in both height and width.

'D Delta' is distinguishable from the female parent plant, by the following characteristics:

1. x *Gasteraloe* 'D Delta' exhibits a smaller number of leaves than the number of leaves of the female parent plant.
2. x *Gasteraloe* 'D Delta' exhibits a flatter overall plant shape than the female parent plant. In contrast, the plant shape of the female parent plant is more erect.

3. x *Gasteraloe* 'D Delta' exhibits leaves that have orbicular dots that are smaller in size than the dots on leaves of the female parent plant.
4. x *Gasteraloe* 'D Delta' exhibits leaf margins with smaller teeth than the teeth of leaf margins of the female parent plant.

'D Delta' is distinguishable from the male parent plant by the following characteristics:

1. x *Gasteraloe* 'D Delta' exhibits a smaller number of leaves than the number of leaves of the male parent plant.
2. x *Gasteraloe* 'D Delta' exhibits shorter leaves than the leaves of the male parent plant.
3. x *Gasteraloe* 'D Delta' exhibits leaves that have fewer orbicular dots than the leaves of the male parent plant.
4. x *Gasteraloe* 'D Delta' exhibits leaf margins with small teeth. In contrast, the leaf margins of the male parent plant have no teeth.
5. x *Gasteraloe* 'D Delta' exhibits a star shaped basal rosette plant shape. In contrast, the male parent plant does not have a rosette plant shape.

BRIEF DESCRIPTION OF THE DRAWING

The accompanying photograph illustrates the distinguishing traits of x *Gasteraloe* 'D Delta'. The photograph shows an overall view of a 24 week old plant.

The photograph was taken using conventional techniques and although colors may appear different from actual colors due to light reflectance, it is as accurate as possible by conventional photographic techniques.

BOTANICAL DESCRIPTION OF THE PLANT

The following is a detailed description of the new x *Gasteraloe* cultivar named 'D Delta'. Data was collected in Amposta, Tarragona, Spain from 24 week old plants grown in a glass greenhouse in 8.5 cm. diameter containers. The time of year was spring and the temperature range was 18-26 degrees Centigrade during the day and 11-21 degrees Centigrade at night. The light level was natural light level. No photoperiodic treatments or growth retardants were used. Color determinations are in accordance with The Royal Horticultural Society Colour Chart 2015 edition, except where general color terms of ordinary dictionary significance are used. The growing requirements are similar to the species. 'D Delta' has not been tested under all possible conditions and phenotypic differences may be observed with variations in environmental, climatic, and cultural conditions, however, without any variance in genotype.

Botanical classification: x *Gasteraloe* hybrid 'D Delta'.
Annual or perennial: Perennial.
Parentage: 'D Delta' is a hybrid of the female parent, an unnamed *Aloe aristata* cultivar and the male parent, an unnamed *Gasteria carinata* var. *verrucosa* cultivar.
Plant type: Potted plant.
Growth habit: Basal rosette, freely producing secondary rosettes.
Plant shape: Flattened globe shaped.
Suitable container size: 5.5 cm pots and larger.
Plant height: Average 10.2 cm.
Plant width: Average 11.5 cm.
Vigor: Moderate.
Low temperature tolerance: 10° Centigrade.
High temperature tolerance: 35° Centigrade.
Propagation: Leaf cuttings.
Time to initiate roots (summer): 19 days at 22° C.
Time to initiate roots (winter): 30 days at 22° C.
Time to produce a rooted cutting (summer): 33 weeks at 22° C.
Time to produce a rooted cutting (winter): 40 weeks at 20° C.
Growth rate: Low to moderate.
Crop time: Approximately 52 weeks.
Root system: Fine and fibrous.
Plant fragrance: None.
Branching habit: Leaves arise in single main basal rosette, freely producing secondary rosettes or plantlets, average of 12 secondary rosettes.
Pinching: Not required.
Foliage:

*Leaf arrangement*.—Basal rosette.
*Compound or single*.—Single.
*Quantity of leaves per plant*.—Average 18.
*Leaf shape*.—Lanceolate, succulent.
*Leaf aspect*.—Flattened.
*Leaf apex*.—Long apiculate.
*Leaf base*.—Broad cuneate.
*Leaf dimensions*.—10.3 cm. in length, 2.3 cm. in width and 0.9 cm. in thickness.
*Leaf texture upper surface*.—Pustulate, moderately covered with small orbicular raised dots 1.5 mm. in diameter and 1.5 mm. in height, color varies between 148D and 157A.
*Leaf texture lower surface*.—Pustulate, moderately covered with small orbicular raised dots 1.0 mm. in diameter and 1.5 mm. in height, color varies between 157C and 157D.
*Leaf luster* (*both surfaces*).—Moderately glossy.
*Leaf rugose* (*both surfaces*).—Not rugose.
*Pubescence* (*both surfaces*).—Absent.
*Leaf margin*.—Finely serrate teeth, teeth 1.0 mm. in length, color N155A.
*Venation pattern*.—None visible.
*Young leaf color* (*upper surface*).—In between 139A and 147A, toward base 146D.
*Young leaf color* (*lower surface*).—In between 139A and 147A, toward base 146D.
*Mature leaf color* (*upper surface*).—In between 147A and N189A, toward base 148B.
*Mature leaf color* (*lower surface*).—In between 139A and 147A, toward base 147B to 147C.

Flower: 'D Delta' has not produced flowers to date.
Fruit and seed: 'D Delta' has not produced fruit or seed to date.
Disease and pest resistance: Disease and pest resistance has not been observed.

The invention claimed is:

1. A new and distinct variety of x *Gasteraloe* plant named 'D Delta' as described and illustrated.

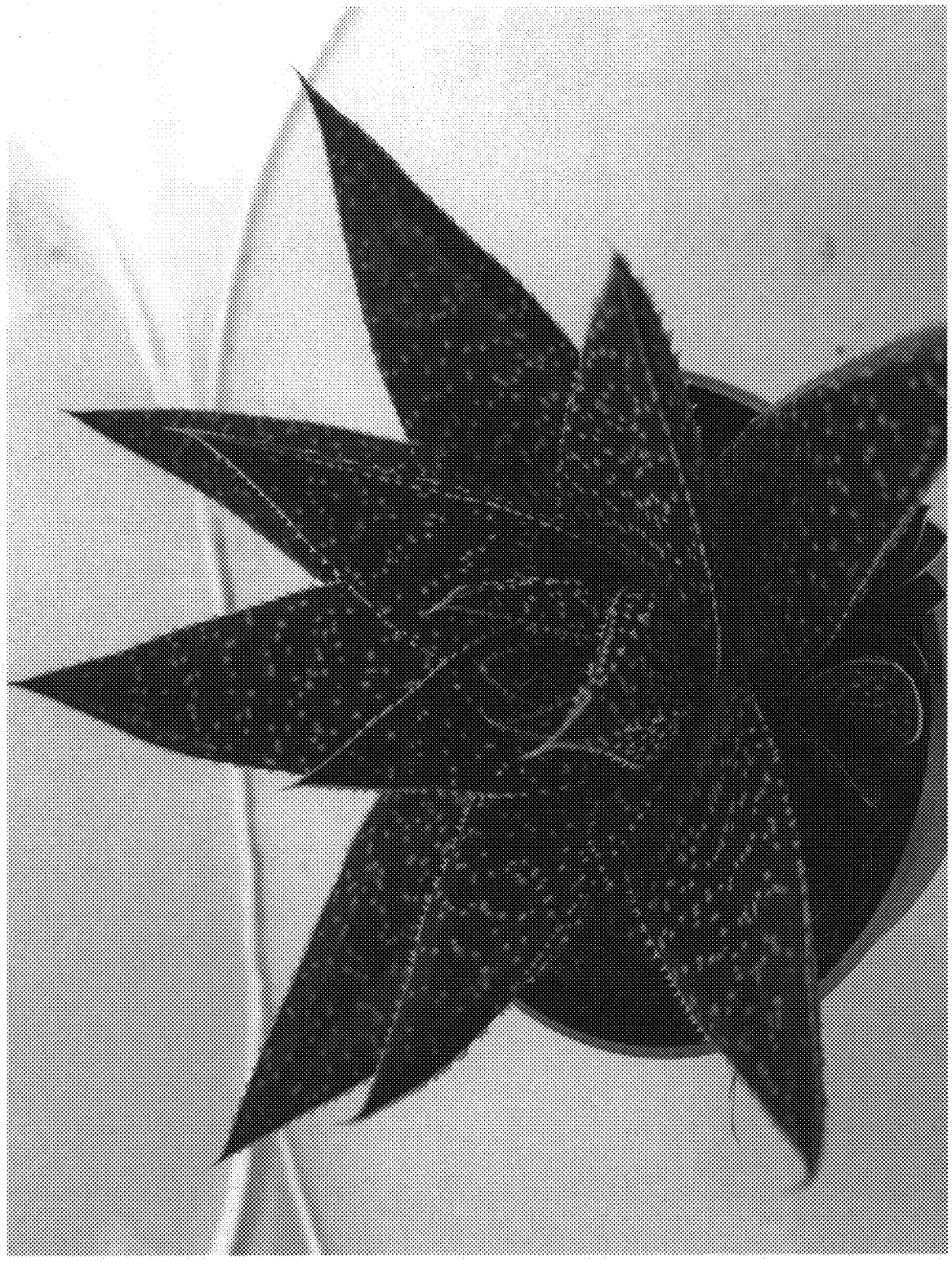

* * * * *